United States Patent [19]
Colombo et al.

[11] 3,953,739
[45] Apr. 27, 1976

[54] METHOD AND APPARATUS FOR THE CONTINUOUS MONITORING AND CONTROL OF CELL SIZE IN A FOAM STRUCTURE

[75] Inventors: Edward A. Colombo, Fairport; James Tarng Tsai, Canandaigua, both of N.Y.

[73] Assignee: Mobil Oil Corporation, New York, N.Y.

[22] Filed: Sept. 30, 1974

[21] Appl. No.: 510,666

[52] U.S. Cl. .............................. 250/571; 250/226; 264/40; 356/209
[51] Int. Cl.² ....................................... H01J 39/12
[58] Field of Search ........... 264/40; 250/223 R, 226, 250/574, 223 PC, 571, 572; 356/102, 103, 104, 209, 210, 119, 120

[56] References Cited
UNITED STATES PATENTS

| | | | |
|---|---|---|---|
| 2,891,722 | 6/1959 | Nuttall et al. | 356/102 |
| 3,368,007 | 2/1968 | Palmer | 264/40 |
| 3,646,188 | 2/1972 | Campbell | 264/40 |
| 3,695,765 | 10/1972 | Bol et al. | 356/102 |
| 3,797,937 | 3/1974 | Shofner | 250/574 |

Primary Examiner—Alfred E. Smith
Assistant Examiner—D. C. Nelms
Attorney, Agent, or Firm—Charles A. Huggett; James D. Tierney

[57] ABSTRACT

A method and apparatus are provided to continuously monitor and measure the average size of individual foam cells contained in a foam structure, such as polystyrene foam for example, as it is being fabricated. Such an arrangement permits the prompt adjustment of process conditions and/or the concentration of nucleating agents in the extrusion system in the event the foam cell size deviates from a preselected norm. The method comprises illuminating the surface of a foam sheet, receiving and collecting at least a portion of the light which is diffused and reflected from the foam sheet with a detector photocell, electrically measuring the amount of light energy received by the photocell and converting such measurements into a cell size measurement.

2 Claims, 5 Drawing Figures

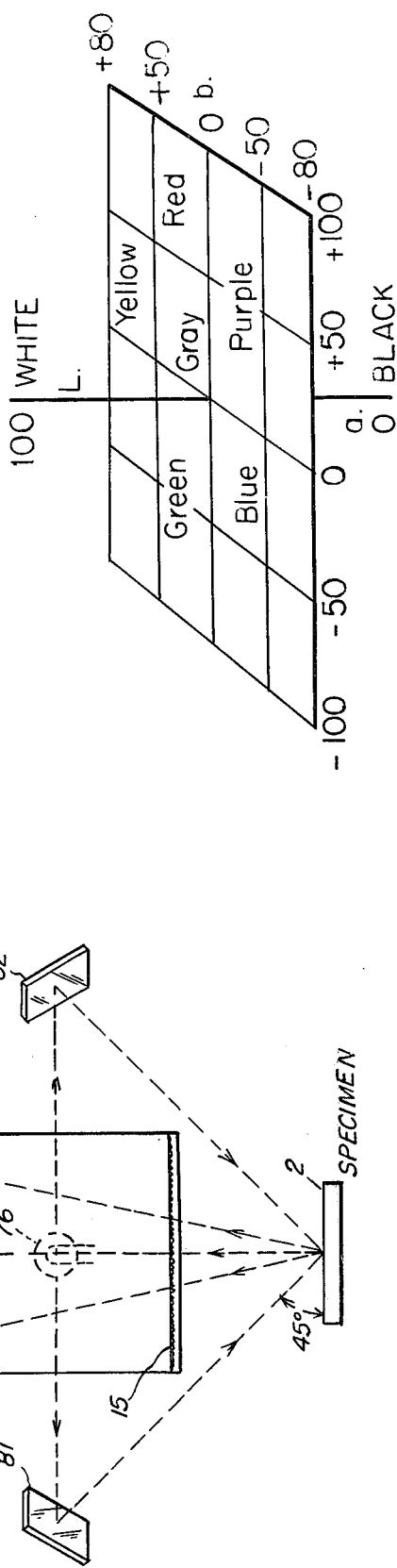
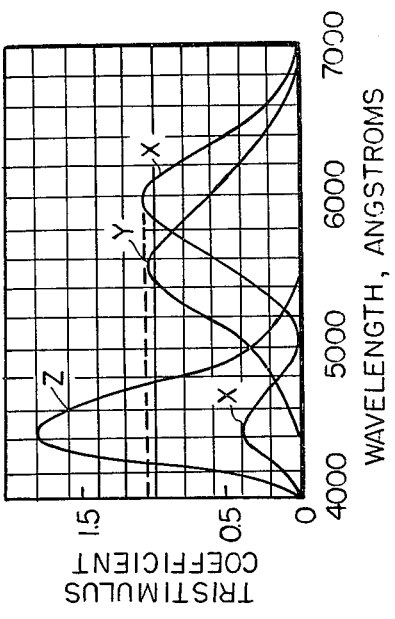
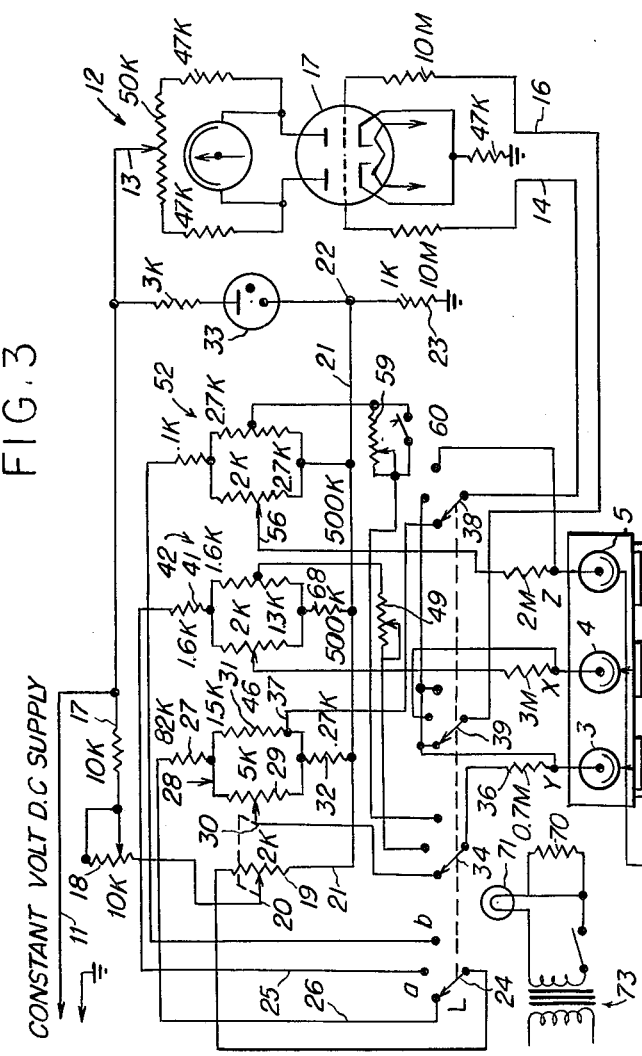

Cell radius (mils)

METHOD AND APPARATUS FOR THE CONTINUOUS MONITORING AND CONTROL OF CELL SIZE IN A FOAM STRUCTURE

BACKGROUND OF THE INVENTION

1. Field of the Invention

The present invention relates to a method and apparatus which employ reflected light to continuously measure the individual cell size of cells contained in an extruded plastic foam product such as polystyrene foam. By continuously monitoring this foam characteristic, the variation of which has a pronounced effect upon the physical properties of the foam, prompt processing and/or material feed (e.g., blowing agent, nucleating agent, etc.) adjustments may be made to bring the cell size back into a specified range in the event that it deviated therefrom.

2. Description of the Prior Art

It is known in the prior art that during the extrusion of polymer foam, cell size is the structural parameter which can be modified most readily and, furthermore, has a pronounced effect on the foam's properties. These properties include compressive strength, tensile strength, elongation at break, tear strength and thermal insulating values. Cell size can be varied by orders of magnitude in a full scale production process by manipulating the necessary process parameters, nucleating agent, melt temperature, and so forth. The quantification of cell size is under normal circumstances tedious and time consuming. Normally a thin section of foam is prepared using a suitable cutting device, microtome or its equivalent. The sample is then examined under a microscope or other suitable device and an attempt is made to characterize the cell size by measuring the mean diameter of the cell or counting the number of cells contained in a given area. Obviously, these prior art methods do not lend themselves to continuous monitoring nor do they necessarily reflect the average cell size of the sample under investigation, since distribution of cell sizes occurs in most foam polymer systems and single point measurements cannot always be translated into an average measurement. In addition, these kinds of cell size quantification can be costly in a production situation. Poor quality and/or "off-specification" material can be manufactured for long periods of time while an out-of-line cell size measurement is being made. Accordingly, it is an object of the present invention to provide a continuous in-line method and apparatus for determining the cell size of polymeric foams as they are extruded. Further, the present invention provides an arrangement whereby in the event the monitored cell size of the foam is not within product specifications, automatic adjustments may be made to extrusion line conditions and/or to the extrusion feed materials to bring the cell size of the foam material within the desired specifications.

SUMMARY OF THE INVENTION

The present invention relates to an apparatus and method for determining the average individual cell size of a plastic foam structure which comprises illuminating the surface of said foam, receiving and collecting at least a portion of the light which is diffused from said foam with a detector photocell, electrically measuring the amount of light energy received by said photocell whereby said light energy measurement is directly converted to said cell size.

BRIEF DESCRIPTION OF THE DRAWINGS

FIG. 1 is a schematic diagram of a rectangular color solid.

FIG. 2 is a plot of the International Committee on Illumination [ICI] of the primary stimuli of specified proportions of light of certain wave lengths.

FIG. 3 is a schematic circuit diagram of a colorimeter which may be employed in the practice of the present invention.

BRIEF DESCRIPTION OF SPECIFIC EMBODIMENTS

Figure 4:
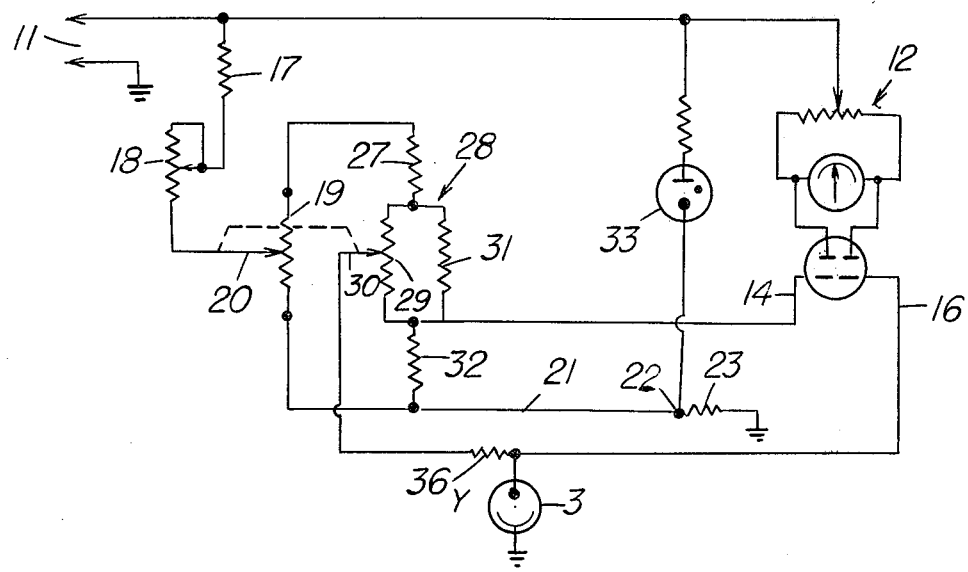
FIG. 4 is a simplified schematic circuit diagram showing the circuit of FIG. 3 with the selector switch in the L position.

In accordance with the present invention it has been found that polystyrene foam material which has a relatively small cell size, e.g., on the order of about 0.25 to 0.75 mil cell size radius appears to have a relatively lighter color then polystyrene foam, which is constituted by individual cells which have a relatively larger cell size, e.g., on the order of from about 1 to 10 mils cell size radius. Accordingly, it was concluded that as the size of the individual cells in a foam structure change such change in size will have a corresponding effect on the shading of the color of the foam structure, i.e., cause it to become lighter or darker. It was further concluded that if a method could be devised whereby such changes and shading of a continuously advancing foam material could be detected by a monitoring device, corrective measures could be taken in the event cell size of the foam may depart from desired limitations.

Techniques for the extrusion of polystyrene foam are well known in the art and a particularly desirable method is disclosed in U.S. Pat. No. 3,482,006, the disclosure of which is incorporated herein by reference. Generally, prior to extrusion, polystyrene pellets are coated with or admixed with a nucleating agent. Typical of such nucleating agents is a mixture of sodium bicarbonate and citric acid although others may be employed. The nucleating agent which is admixed with the polystyrene serves to control the cell size of the cells contained in the extruded foam product. Following admixing of the nucleating agent with the polystyrene resin, the mixture is fed to a standard rotating screw type extruder, wherein it is thoroughly mixed and melted as it is advanced towards the exit end of the extruder. A blowing agent such as pentane or isopentane is injected into the extruder downstream of the feed hopper. The pentane blowing agent is thoroughly admixed with the melted polystyrene and nucleating agent and this mixture is eventually extruded from the extrusion system through a die, either in the form of a flat foam sheet or a tubular structure which is subsequently cooled, and the polystyrene foam sheeting recovered. As hereinbefore discussed, it is of prime importance that the size of the individual cells of the foam structure be regulated within close tolerances. Cell size variation in a finished foam product has a pronounced effect on the properties of the foam structure. Although foam cell size may be controlled or rather varied by varying process parameters, the prime control means for adjusting foam cell size is usually by control of the concentration of nucleating agents in the extrusion system. This concentration however, during continuous extrusion processes, may vary somewhat due to the vagaries of the system such as erratic feed at the nucleant feed hopper, incomplete or non-uniform mixture of the nucleants with the resin, and other undesirable conditions. Applicants have now found that irregularities in the size of the cell in the extruded foam sheet may be continuously monitored and quickly discovered and corrected by continuous measurement of the color, i.e., color shading differences of the foam sheet.

In general, color may be specified by assigning numerical values to the quantity of each wavelength of light in that color. However, these numerical values are cumbersome and not readily useful because values representing the humanly observed properties of colors are obtainable from them only by extensive calculation. As a result of establishment by the International Committee on Illumination (ICI) of three primary stimuli with which any color in the humanly visible spectrum can be matched, any humanly visible color can be specified in in terms of the quantities of these stimuli. FIG. 2 of the drawings is a plot of the ICI primary stimuli. Each of these primary stimuli is an assembly of specified proportions of light of certain wavelengths and represents the maximum of a family of curves. The X curve represents an essentially red stimulus, the Y curve an essentially green stimulus, and the Z curve an essentially blue stimulus.

Any color can be represented by a curve in each family. Ordinates of the maximums of the curve in each family are the tristimulus coefficients of the color. The Y curve was selected by ICI so the plot of the proportion versus wavelength corresponds to the light sensitivity curve of the normal human eye; the ordinate of the Y curve of the color, corrected for the intensity of the illuminating sourve, identifies the intensity of the color. The hue and the saturation of the color can be readily calculated from its tristimulus coefficients by using the chromaticity diagram described by Margenau, Watson and Montgomery, Physics Principles and Applications 673–677 (2nd Edition, McGraw-Hill Book Co., New York, 1953).

In the conventional psychological color solid representing the color of surfaces, the vertical axis represents the lightness which varies from black to white through the various degrees of grayness. The hue is represented by the direction from the axis, the various directions corresponding to red, yellow, green, blue, purple or intermediate colors; and the saturation is represented by the length of the radius extending from the gray or lightness axis to the periphery representing the strongest colors. FIG. 1 illustrates a commonly used arrangement for depicting colors in terms of three values, generally corresponding to those of the conventional color solid, but conforming to a three dimensional Cartesian coordinate system. An arbitrary scale of values is assigned to each coordinate as shown. The system of color classification and designation employed in the commercially available color difference meter used in the following examples (Hunter-Model D25 Color and Color-Difference Meter) is based upon the rectangular solid color shown in FIG. 1. As can be seen from FIG. 1, the L scale ranges from 0–100 (black to pure white). This scale is related to the reflectance of a sample and is used, for purposes of the following specific embodiments of the present invention, to correlate cell size and scattered light.

The following is a brief description of the circuitry used in the hereinbefore described colorimeter employed in obtaining the measurements used in the following examples. FIG. 3 illustrates a schematic circuit diagram showing the principle of operation.

The equations to be solved are: $L = k_1 \sqrt{Y}$, $a = k_2 (X-Y) \sqrt{Y}$, $b = k_3 (Y-Z) \sqrt{Y}$, in which $a$ indicates RED when plus and GREEN when minus, and $b$ indicates YELLOW when plus and BLUE when minus. $k_1$, $k_2$ and $k_3$ are constants which are controlled by the various resistance ratios in the circuit. When measuring color difference, the instrument computes the difference in the $L$, $a$ or $b$ ($X$, $Y$ or $Z$) values of the standard and sample. The equation is sample - standard. The values of $X$, $Y$ and $Z$ run from zero, with no light on the phototube, to 100 when an ideal white diffuser (reflectance = 100%) is being measured.

In the optical head, light is received by the phototubes through optical filters which control the spectral character of the light. The currents generated by the phototubes are protional tristimulus functions $X$, $Y$ and $Z$. The flow of this current into operational amplifiers, in the optical head, generates voltage signals proportional to the tristimulus functions. These signals are routed to the difference amplifier board in the measurement unit where the photodetector dark currents are corrected for, and the $k_2 (X-Y)$ and $k_3 (Y-Z)$ computations are made. Five signals from this board ($X$, $Y$, $Z$, $k_2(X-Y)$ and $k_3 (Y-Z)$) are routed to the selector switches. The $Y$ signal is also routed to the square root board where $\sqrt{Y}$ is computed and routed to the selector switches. The selector switches enable the operator to select the function to displayed, i.e., $L$, $a$ or $b$.

Referring to FIG. 3, the specimen 2, which is being measured is illuminated with light from a suitable source 76, at an angle of 45° in the case of a reflecting specimen (as contrasted with a light transmitting specimen), through a suitable diffusing plate 15. A practical exposure unit uses a low voltage halogen cycle lamp calibrated with a lamp voltage of approximately 9.75 volts to produce a known color temperature. The lamp in combination with lenses and mirrors produce 2 beams so as to strike the surface of the specimen from opposite directions at angles of 45°, as shown in FIG. 3. Light reflected from the specimen in perpendicular and near perpendicular directions is measured by photocells 3, 4 and 5, giving respectively the $Y$, $X$ and $Z$ signals by virtue of tristimulus light filters 7, 8 and 9 placed between the photocells and the light reaching them.

The degree to which photocell 3 is stimulated by the reflected light from the specimen is used as an indication of the lightness factor L; similarly cell 4 is used to provide (in combination with cell 3) a signal which is a function of the RED-GREEN factor $a$; and cell 5 is used in the same manner for the YELLOW-BLUE factor $b$, referring to the schematic diagram of FIG. 1.

Referring again to FIG. 3, the circuits used are energized by a constant voltage D-C. supply 11, to which is connected a difference potentionmeter 13 for zero setting of the instrument. The meter is fed signals form two signal lines 14 and 16 through a dual-triode 17, the grids of which are connected to the respective signal lines, while their plates are connected to their respective meter inputs, whereby the meter is initially adjusted by potentiometer 13 to zero scale position and thereafter measures the differences between the D.C. voltage levels of the signals supplied to it by lines 14 and 16.

The ungrounded side of line 11 is also connected through a fixed resistor 17 and an adjustable resistor or potentiometer 18 to the slider of a reference potentiometer 19. One end of potentiometer 19 is connected through line 21 to point 22 and thence through a fixed resistor 23 to ground. The other end of potentiometer 19 is connected through the L setting of selector switch 24 to line 26 and thence through resistor 27 to a bridge arrangement 28 consisting of a potentiometer 29 and fixed resistor 31 connected in parallel as shown.

The lower common end of bridge 28 is connected through resistor 32 to lead 21. A gas-tube regulator 33 is connected between point 22 and line 11 to aid in regulating and in maintaining essentially constant current through resistance 23 in the face of adjustments of potentiometer 18. This voltage regulation is necessary in order to hold phototube voltages and grid voltages in the tube 17 nearly constant. The slider 30 of potentiometer 29 is connected through selector switch 34, in the L position shown in FIG. 3, to a load resistor 36 connected to the anode of photocell 3. Line 14 of the difference meter is connected to the common point of resistors 29 and 32 via line 37 and switch 38 while line 16 of the meter is connected via switch 39 to point Y, which is at the anode potential of tube 3.

The elements above described are essentially all of the circuit elements involved in the L setting of switch 24, that is, the setting used in obtaining the value of L, which, as was indicated above, is one of the three values needed to identify a color. These elements are separated out from the rest of the circuit and redrawn in FIG. 4 in order to show more clearly the circuits used in obtaining the L value. The same reference characters are employed as in FIG. 3 to facilitate comparison of the two circuit drawings.

Referring to FIG. 4, it should be noted that this circuit is arranged as a substantially constant current circuit, so far as the effect of variation of the sliders of reference potentiometer 19 and Y balance potentiometer 29 are concerned. These two sliders are ganged; that is, they are fixed to move together so that they are both always at the same relative position on their respective resistance windings. However, due to the high series resistance of element 17 and the low resistance bridging elements 27 and 32 as well as the parallel bridging paths presented by the resistors 31 and 29, it will be apparent that as sliders 20 and 30 move along their respective resistance elements, the total current flow through slider 20 will remain substantially constant, since the net series resistance variation introduced by movement of the sliders in the bridging circuit shown is negligibly small. The circuit thus functions, in effect, as a constant current bridge, and for all practical purposes, the current through slider 20 may be considered as a constant current. The bridge is adjusted by varying the position of ganged sliders 20 and 30 until the difference meter reads zero, that is, the voltage drop across load resistor 36 of photocell 3 is balanced out. When this balance has been obtained, the scale setting is noted which corresponds to the distance from point zero of potentiometer 29 to the slider; this distance gives the value of Y , which corresponds to the desired reading for the value L. Similar circuits are described in U.S. Pat. No. 3,003,388, the disclosure of which is incorporated herein by reference.

The colorimeter, as aforedescribed, can be calibrated to produce tristimulus coefficients directly or it can be used to measure color differences between a standard and a material. When used to measure differences, standardization of the colorimeter is accomplished by obtaining tristimulus coefficients of the color standard. For maximum sensitivity a standard having color characteristics as close as possible to the material is used. When the colorimeter is used for determination of cell size in a thermoplastic foam product, standards preferably have the color characteristics of the foam product under examination. Once coefficients of a color standard have been recorded, the colorimeter may be easily recalibrated to that standard. When measuring the size of cells contained in white unpigmented polystyrene foam the value given by the L scale of the colorimeter (i.e., the scale which registers a value corresponding to a samples' lightness or darkness) is the only scale which it is necessary to employ. A black background is employed for mounting the polystyrene foam specimen being examined.

In the following Table I data is presented for a series of examples wherein the reading on the aforedescribed L scale is correlated with the individual cell size in a series of polystyrene foam samples. It will be noted how the cell size varies dependent on the concentration of nucleating agents employed, an increase of the nucleating agents concentration in the extrusion system resulting in the production of foam having a smaller individual cell size and vice-versa. The nucleating system employed to produce the individual foam samples in the following examples of Table I was a mixture of anhydrous citric acid and sodium bicarbonate, the bicarbonate being present in a weight ratio to the acid of about 1:0.76. The polystyrene resin employed was identified by the manufacturer as Dow-685 general purpose polystyrene. The extrusion apparatus employed to produce the foam samples is described in U.S. Pat. No. 3,482,006.

EXAMPLE 1

Polystyrene resin pellets were admixed with a nucleating agent mixture comprising sodium bicarbonate and anhydrous citric acid. The nucleating agents constituted 0.58% by weight based upon the total weight of the polystyrene feed charge. The acid to bicarbonate ratio was 1:0.76. These materials were continuously fed into the feed hopper of a 2½ inch diameter screw extruder having a L/D ratio of 24:1. The extruder was operated at an extrusion rate of 150 lb./hr. and the extruder screw was internally cooled with water at a temperature of about 72°F. By means of extruder barrel heaters, the portion of the extruder barrel surrounding the feed zone of the extruder was maintained at a temperature of about 220°F. In the melting zone, pentane injection zone, and the mixing zone, the extruder barrel was maintained at a temperature of from about 400° to 450°F. A liquid pentane blowing agent was injected through the extruder barrel, about 5% by weight of pentane based upon the total weight of resin and nucleating agent, and into the polystyrene composition at a point beyond the feed section where the polystyrene was in a molten condition. The molten mass was than passed through the extruder mixing zone and finally through the cooling section of the extrusion system before being extruded through an annular die orifice, affixed to the terminal end of the extruder.

Samples of the foam produced in accordance with the foregoing example were then measured with the colorimeter; hereinabove described, to obtain their L value. The size of the individual foam cells in the foam sample were then physically measured under magnification (100 ×).

The procedure of Example 1 was employed to produce additional samples in Examples 2 through 13 inclusive, the concentration of nucleating agents being varied, as shown in the following Table I.

TABLE I

CORRELATION OF "L" READING WITH AVERAGE CELL RADIUS

| Example | L | (in.) Gauge | gm/cc Density | (Mils) Cell Radius | % Nucleating Agents |
|---|---|---|---|---|---|
| 1 | .9180 | .101 | .066 | 3.08 | .58 |
| 2 | .9142 | .098 | .070 | 3.18 | .51 |
| 3 | .8936 | .096 | .072 | 3.82 | .43 |
| 4 | .8786 | .088 | .079 | 4.55 | .34 |
| 5 | .8940 | .085 | .079 | 4.01 | .38 |
| 6 | .9297 | .096 | .070 | 2.69 | .58 |
| 7 | .9296 | .110 | .062 | 2.81 | .58 |
| 8 | .9109 | .093 | .071 | 3.11 | .49 |
| 9 | .9119 | .095 | .067 | 2.78 | .57 |
| 10 | .9283 | .097 | .068 | 2.56 | .65 |
| 11 | .9338 | .100 | .066 | 2.19 | .74 |
| 12 | .9411 | .101 | .066 | 1.78 | .82 |
| 13 | .9348 | .100 | .065 | 1.86 | .89 |

Figure 5:
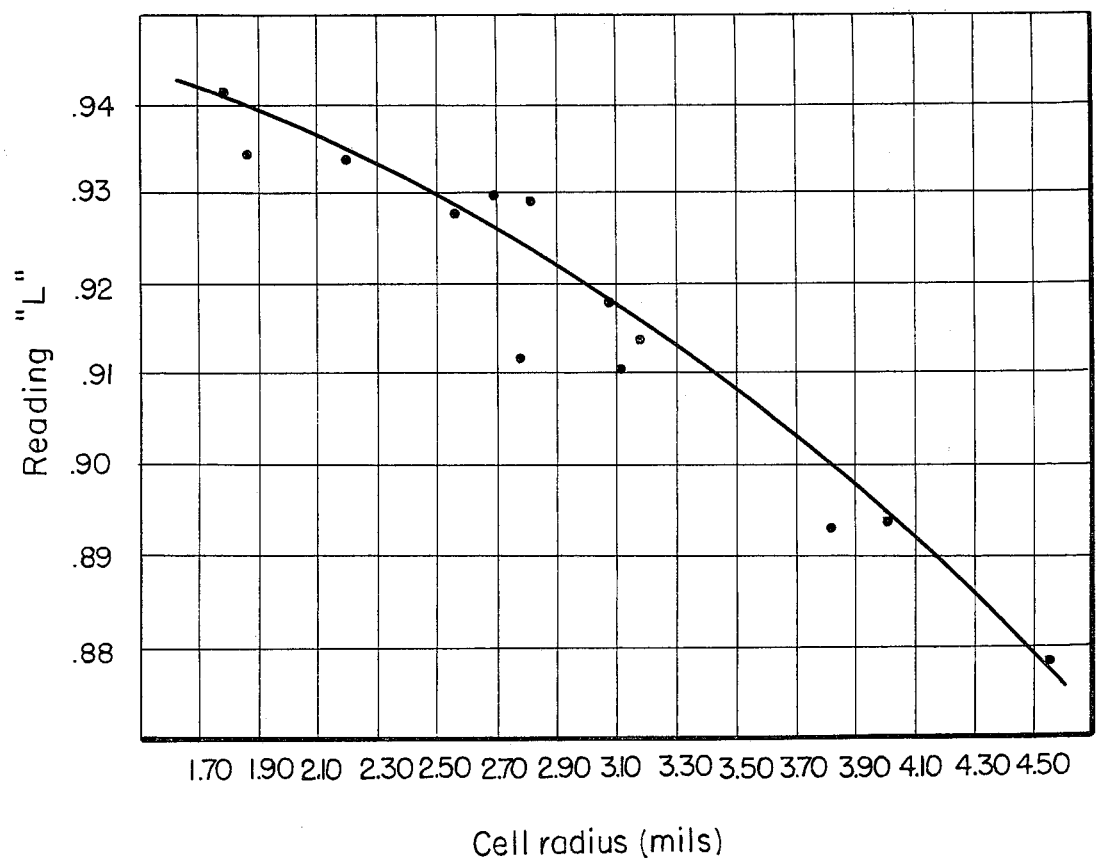
FIG. 5 is a plot of individual foam cell size radius versus L values.

As shown in FIG. 5, the data obtained from the preceeding examples was plotted to obtain a master curve, correlating the L reading from the colorimeter with the cell radius of individual cells in the foam samples. It will be noted that, in accordance with the data, as the amount of nucleating agent was varied the size of the cells changed, i.e., increasing the nucleating agent concentration resulted in a decrease in the foam cell radius and vice versa. By employing the master curve shown in FIG. 5, it is now possible to obtain the L value of a given foam sample utilizing the colorimeter and translate that L value directly to the size of the foam cells in the sample. Obviously, this may be done either out of line or preferably in line. For example, the colorimeter was easily mounted above the continuous running web of polystyrene foam and the L value of the foam was continuously registered on the colorimeter digital readout. This measurement may be continuously recorded on an advancing recording chart. Whenever it appeared that the L value was either too high or too low with respect to the particular cell size desired, a simple adjustment was made, automatically (e.g., by computer control) if desired, to either increase the concentration of the nucleating agent being admixed with the resin prior to introduction of the mixture into the extrusion system. As hereinbefore noted, it is also possible to vary other process parameters to obtain variation in cell size such as, for example, density, blowing agent concentration, melt temperature and others.

What is claimed is:

1. A method for determining the average individual cell size of a plastic foam sheet which comprises illuminating the surface of said foam, receiving and collecting at least a portion of the light which is diffused from said foam with a detector photocell, electrically measuring the amount of light energy received by said photocell whereby said light energy measurement is directly converted to said cell size.

2. A method in accordance with claim 1 wherein said foam is continually advancing, said cell size measurement being taken in a continuous in-line operation.

* * * * *